United States Patent [19]

Karami

[11] 3,948,258
[45] Apr. 6, 1976

[54] DIAPER TAPE FASTENER
[75] Inventor: Hamzeh Karami, Crystal Lake, Ill.
[73] Assignee: Colgate-Palmolive Company, New York, N.Y.
[22] Filed: Feb. 24, 1975
[21] Appl. No.: 552,584

[52] U.S. Cl. .................. 128/287; 128/284; 24/67 R
[51] Int. Cl.² A43C 11/00; A41B 13/02; A61F 13/16
[58] Field of Search .......... 128/284, 287, 286, 296; 24/67 R, 67 AR

[56] References Cited
UNITED STATES PATENTS

| | | | |
|---|---|---|---|
| 3,620,217 | 11/1971 | Gellert | 128/284 |
| 3,646,937 | 3/1972 | Gellert | 128/287 |
| 3,776,234 | 12/1973 | Hoey | 128/287 |
| 3,810,472 | 5/1974 | Aldinger et al. | 128/287 |
| 3,848,594 | 11/1974 | Buell | 128/284 |
| 3,875,621 | 4/1975 | Karami | 24/67 |

Primary Examiner—Aldrich F. Medbery
Attorney, Agent, or Firm—Powell L. Sprunger

[57] ABSTRACT

A tape fastener for a disposable diaper having opposed surfaces and opening means extending through the diaper. The tape fastener has a pressure-sensitive tape strip having a first portion secured to one surface of the diaper with adhesive on the first portion being exposed through the opening means. The fastener also has a release sheet having at least a portion secured to the other surface of the diaper by the adhesive exposed through the opening means.

20 Claims, 10 Drawing Figures

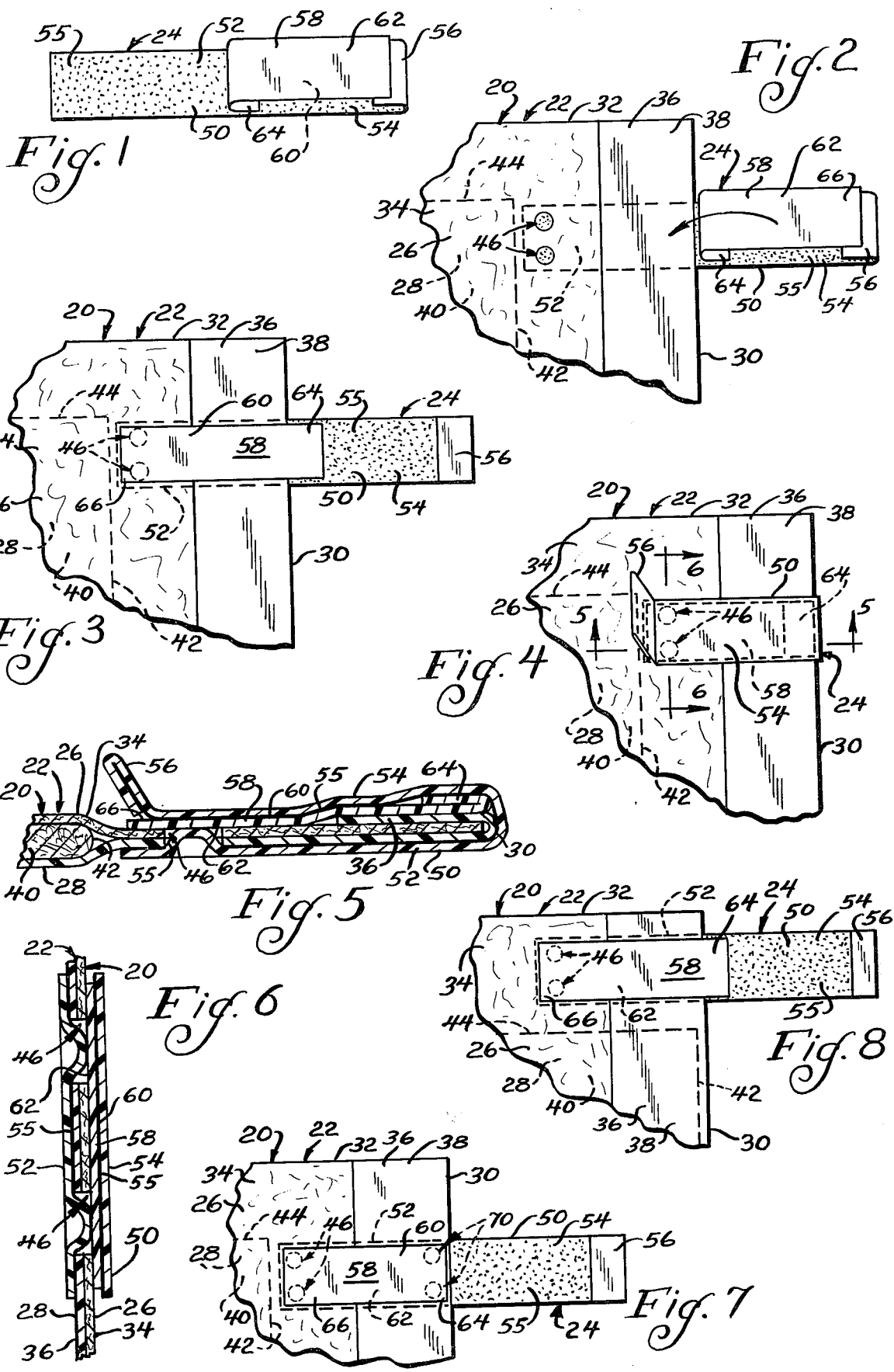

DIAPER TAPE FASTENER

BACKGROUND OF THE INVENTION

The present invention relates to absorbent articles, and more particularly to disposable diapers.

A various assortment of disposable diapers have been proposed for use on infants. A number of such diapers have been provided with tape fasteners for securing the diaper about the infant during placement. The tape fasteners have generally taken the form of a tape strip having a securement portion which is covered by a release sheet, with the release sheet being removed from the securement portion of the tape strip during placement of the diaper to expose adhesive on the securement portion. While it has been found that parents prefer that the release sheet be secured to the diaper itself to eliminate the necessity for discarding the release sheet, it is also desirable that the tape fastener be made of economic construction to reduce the cost of the diaper to the consumer.

SUMMARY OF THE INVENTION

A principal feature of the present invention is the provision of a tape fastener for a disposable diaper of simplified construction and reduced cost.

The diaper has an absorbent pad assembly having an absorbent pad, a back surface, a front surface, at least one side edge, and opening means extending through the pad assembly and spaced from the side edge. The tape fastener comprises, a pressure-sensitive tape strip having a first end section secured to the back surface of the pad assembly with adhesive on the first end section being exposed through the opening means of the pad assembly, and a second securement end section extending past the side edge of the pad assembly. The tape fastener also has a sheet, such as a release sheet, having a first surface providing a relatively low affinity for adhesive on the tape strip and having a second surface facing the front surface of the pad assembly, with the second surface having at least a moderate affinity for adhesive on the tape strip. The adhesive exposed through the opening means contacts the second surface of the sheet and retains one end portion of the sheet to the pad assembly.

In one embodiment, the sheet extends from the opening means past the side edge of the pad assembly, with the second surface of the other end of the sheet being secured to adhesive on the second end section of the tape strip. In another embodiment, the pad assembly has second opening means adjacent the side edge of the pad assembly, with adhesive of the first end section of the tape strip being exposed through the second opening means. The adhesive exposed through the second opening means contacts the other end of the sheet adjacent the side edge of the pad assembly, and retains the other end of the sheet against the front surface of the pad assembly.

Thus, a feature of the present invention is that the sheet may be permanently retained against the front surface of the pad assembly, and need not be discarded after placement of the diaper.

Another feature of the present invention is that the sheet is retained against the front surface of the pad assembly by adhesive on the tape strip.

Thus, another feature of the invention is that the sheet is retained against the pad assembly without use of a separate adhesive layer on the sheet.

Further features will become more fully apparent in the following description of the embodiments of this invention and from the appended claims.

DESCRIPTION OF THE DRAWINGS

In the drawings:

FIG. 1 is a perspective view of a tape fastener according to the present invention prior to placement on a diaper;

FIG. 2 is a fragmentary plan view of a disposable diaper showing the tape fastener of FIG. 1 as partially applied to the diaper;

FIG. 3 is a fragmentary plan view of the diaper showing the tape fastener of FIG. 1 as secured to the diaper;

FIG. 4 is a fragmentary plan view of the diaper of FIG. 3 showing a securement portion of a tape strip releasably attached to a release sheet in the tape fastener;

FIG. 5 is a fragmentary sectional view taken substantially as indicated along the line 5—5 of FIG. 4;

FIG. 6 is a fragmentary sectional view taken substantially as indicated along the line 6—6 of FIG. 4;

FIG. 7 is a fragmentary plan view of a diaper showing another embodiment of the tape fastener of the present invention;

FIG. 8 is a fragmentary plan view of another embodiment of the tape fastener and diaper of the present invention;

DESCRIPTION OF THE PREFERRED EMBODIMENTS

Figure 9:
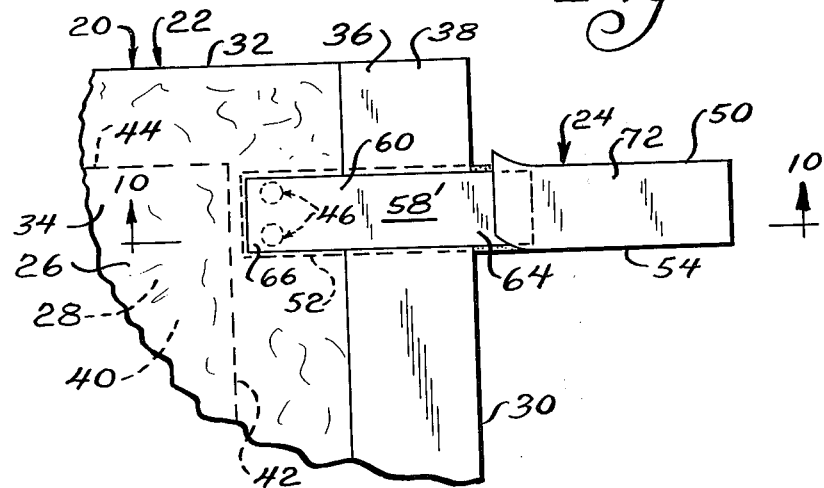
FIG. 9 is a fragmentary plan view of a diaper showing another embodiment of the tape fastener of the present invention.

Referring now to FIGS. 4 and 5, there is shown a disposable diaper generally designated 20 having an absorbent pad assembly 22 and a tape fastener 24 secured to the pad assembly 22. The pad assembly 22 has a front surface 26, a back surface 28, a side edge 30, and an end edge 32 connecting the side edge 30. The pad assembly 22 has a fluid pervious cover sheet 34 defining a substantial portion of the front surface 26 of the pad assembly, a fluid impervious backing sheet 36 defining the back surface 28 of the pad assembly and having a lateral side margin 38 folded over and secured to the front surface 26 of the pad assembly, and an absorbent pad 40 intermediate the cover and backing sheets 34 and 36. The absorbent pad 40 has a side edge 42 spaced from the side edge 30 of the pad assembly 22, and an end edge 44 connecting the side edge 42 and spaced from the end edge 32 of the pad assembly 22. As shown in FIGS. 2–6, the pad assembly 22 also has opening means 46 extending through the pad assembly, and spaced from the side edge 30 of the pad assembly 22. In this embodiment, the opening means 46 comprises a pair of spaced openings which are located intermediate the side edge 42 of the absorbent pad and the side edge 30 of the pad assembly. The openings are spaced longitudinally relative the diaper and laterally across an underlying tape strip, as will be seen below. It is understood that the opposed side of the diaper (not shown) would normally have a structure substantially similar to that described above, and would include a tape fastener as described below.

As shown in FIG. 1, the tape fastener 24 has an elongated pressure-sensitive tape strip 50 having a first end section 52, a second securement end section 54, and adhesive 55 on one surface of the strip. The tape strip 50 may have a folded over end 56 adjacent the outer end of the second end section 54 defining tab means for a purpose which will be described below. The tape fastener 24 also has a release sheet 58 having a first surface 60 providing a relatively low affinity for the adhesive 55 on the tape strip 50, and a second opposed surface 62 having a relatively high affinity for the adhesive 55 on the tape strip 50. The second surface 62 of one end 64 of the release sheet 58 is secured to the adhesive 55 on the second end section 54 of the tape strip 50, in order to retain the one end 64 to the tape strip, as described below. Either the first surface 60 or the second surface 62 of the release sheet 58 may be treated, as desired, to obtain the relative affinities for the adhesive 55. For example, the first surface of a paper strip, serving as the release sheet, may be treated with a silicon release coating to obtain the desired release characteristics from the adhesive, while the second surface remains untreated to obtain a firm bond with the adhesive.

As shown in FIG. 2, the first end section 52 of the tape strip 50 is secured to the back surface 28 of the pad assembly 22, such that adhesive on the first end section 52 is exposed through the openings or opening means 46. As illustrated in FIG. 2 and 3, the other end 66 of the release sheet 58 is folded over the front surface 26 of the pad assembly 22, with the second surface 62 of the release sheet 58 facing the front surface 26 of the pad assembly. Since the side edge 42 of the absorbent pad 40 is spaced from the opening means 46, the relatively thin cover and backing sheets 34 and 36 present only a slight spacing between the other end 66 of the release sheet 58 and the first end section 52 of the tape strip 50. Accordingly, the other end 66 of the release sheet 58 may be pressed against the pad assembly, in order that the adhesive which is exposed through the opening means 46 contacts the second surface 62 of the release sheet 58. Since the second surface 62 of the release sheet 58 has a relatively high affinity for the adhesive 55 on the tape strip 50, the one end 64 of the release sheet 58 is retained by the adhesive on the second end section 54 of the tape strip, while the other end 66 is retained against the front surface 26 of the pad assembly 22 by the adhesive exposed through the opening means 46. Accordingly, the release sheet is retained against the front surface 26 of the pad assembly without use of separate adhesive on the release sheet 58, thus eliminating the cost of the separate adhesive for the release sheet.

As shown in FIGS. 3-6, the second end section 54 of the tape strip 50, including the one end 64 of the release sheet 58, is folded over the front of the diaper and the second end section 54 of the tape strip 50 is releasably attached to the first surface 60 of the release sheet 58. Since the first surface 60 of the release sheet 58 has a relatively low affinity for the adhesive on the second end section 54 of the tape strip, the second end section of the tape strip may be readily removed from the release sheet 58 during placement of the diaper. Removal of the second end section 54 from the release sheet 58 is facilitated by the tab 56 at the outer end of the second end section, which is free of attachment to the release sheet 58 or the pad assembly 22. After the second end section 54 of the tape strip 50 is removed from the first surface 60 of the release sheet 58, in the position as shown in FIG. 3, the second end section is properly located for securing the diaper 20 about the infant. Thus, securement of the diaper is accomplished without removal of the release sheet from the pad assembly, eliminating the necessity for separately discarding release sheets after placement of the diaper.

However, if desired, the second surface 62 of the release sheet or connecting strip 58 may be treated to provide a moderate affinity toward the adhesive 55 on the tape strip 50. In this configuration, the release sheet or anchoring strip 58 is retained in place during normal use of the diaper, as previously described. The user may peel the release sheet 58 from the diaper to expose fresh adhesive which was covered by the one end 64 of the release sheet 58. The fresh adhesive may be utilized to reposition the tape strip during further use of the diaper, or to secure the diaper in a rolled or folded configuration after use of the diaper for convenient disposal of the soiled diaper.

Another embodiment of the present invention is illustrated in FIG. 7, in which like reference numerals designate like parts. In this embodiment, the side edge 42 of the absorbent pad 40 is spaced from the side edge 30 of the pad assembly 22, and the opening means 46 is located intermediate the side edge 42 of the absorbent pad and the side edge 30 of the pad assembly, as previously described. However, in this embodiment, the pad assembly has second opening means 70 extending through the pad assembly and located adjacent the side edge 30 of the pad assembly, with adhesive on the first end section 52 of the tape strip 50 also being exposed through the second opening means 70. In this embodiment, the one end 64 of the release sheet 58 is located adjacent the side edge 30 of the pad assembly 22. Thus, the adhesive exposed through the second opening means 70 contacts the second surface 62 of the one release sheet end 64, and secures the one end 64 against the front surface 26 of the pad assembly 22, while the adhesive exposed through the first opening means 46 retains the other end 66 of the release sheet 58 against the pad assembly. Accordingly, the release sheet 58 is retained in place against the front surface of the pad assembly by the adhesive exposed through the spaced opening means 46 and 70.

Another embodiment of the tape fastener of the present invention is illustrated in FIG. 8, in which like reference numerals designate like parts. In this embodiment, the side edge 42 of the absorbent pad 40 extends to a location adjacent the side edge 30 of the pad assembly 22. Since the bulk of the absorbent pad 40 may make it difficult to secure the release sheet 58 to the first end section 52 of the tape strip through opening means which extends through the pad 40 itself, in this embodiment the tape fastener 24 is located intermediate the end edge 44 of the absorbent pad 40 and the end edge 32 of the pad assembly 22. In this region, the relatively thin thickness of the cover and backing sheets 34 and 36 does not impair attachment of the adhesive on the first end section 52 to the second surface 62 of the release sheet. In other respects, the tape fastener 24 of FIG. 8 is similar to that described in connection with FIGS. 1-6.

Figure 10:
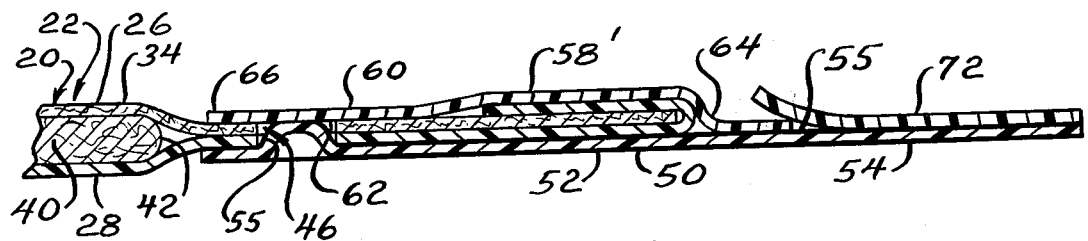
FIG. 10 is a fragmentary sectional view taken substantially as indicated along the line 10—10 of FIG. 9.

Another embodiment of the present invention is illustrated in FIGS. 9 and 10, in which like reference numerals designate like parts. In this embodiment, a release sheet 72 is releasably attached to the adhesive on the second end section 54 of the tape strip 50. The release sheet 72 is removed from the second end section 54 during placement of the diaper to expose the underlying adhesive which is then used to secure the diaper about the infant. In this embodiment, the sheet 58', which need not have a treated first surface 60, serves to obtain improved anchorage of the first end section 52 of the tape strip 50 to the diaper. The sheet 58' is secured to the tape strip 50 through the opening means 46 and at the one end 64 of the sheet 58', thus preventing the first end section 52 of the tape strip 50 from being torn from the back sheet and being pulled away from the diaper. The release sheet described in connection with previous embodiments of the tape fastener also serves a similar function.

The foregoing detailed description is given for clearness of understanding only, and no unnecessary limitations should be understood therefrom, as modifications will be obvious to those skilled in the art.

I claim:
1. A disposable diaper, comprising:
   an absorbent pad assembly having an absorbent pad, opposed first and second surfaces, at least one side edge, and opening means extending through the pad assembly and spaced from said side edge; and
   a tape fastener comprising,
      a pressure-sensitive tape strip having a first end section secured to the first surface of the pad assembly with adhesive on the first end section being exposed through said opening means of the pad assembly, and a second securement section extending past said side edge of the pad assembly, and
      a sheet having a first surface and a second surface facing the second surface of the pad assembly and having at least a moderate affinity for adhesive on said tape strip, with said adhesive exposed through the opening means contacting the second surface of the sheet and retaining at least a portion of the sheet against the pad assembly.

2. The diaper of claim 1 wherein said first surface of said sheet has a relatively low affinity for adhesive on the tape strip, and the second section of the tape strip is releasably attached to the first surface of the sheet.

3. The diaper of claim 2 wherein said second section of the tape strip has tab means adjacent its outer end to facilitate removal of the second section from the sheet.

4. The diaper of claim 1 wherein said sheet extends from said opening means toward the side edge of the pad assembly.

5. The diaper of claim 4 wherein said sheet has one end extending past the side edge of the pad assembly, with said one end of the sheet having its second surface secured to adhesive on the second section of the tape strip adjacent said side edge.

6. The diaper of claim 5 wherein the sheet is releasably attached to the tape strip.

7. The diaper of claim 4 wherein said pad assembly includes aperture means intermediate said opening means and the side edge of the pad assembly, with adhesive on the first end section of the tape strip being exposed through said aperture means and contacting the second surface of the sheet to retain a portion of the sheet against the pad assembly.

8. The diaper of claim 7 wherein one end of said sheet is located intermediate the aperture means and the side edge of the pad assembly.

9. The diaper of claim 7 wherein said aperture means is located adjacent the side edge of the pad assembly.

10. The diaper of claim 1 wherein an end edge of the sheet is located adjacent said opening means and remote the opening means relative the side edge of the pad assembly.

11. The diaper of claim 1 wherein said pad assembly includes a fluid impervious backing sheet defining at least a portion of the first surface of the pad assembly, and in which said first end section of the tape strip is secured to said backing sheet.

12. The diaper of claim 1 wherein said absorbent pad includes at least one side edge spaced from the side edge of the pad assembly, and in which said opening means is located intermediate the side edge of the pad and the side edge of the pad assembly.

13. The diaper of claim 1 wherein said absorbent pad has an end edge spaced from an end edge of the pad assembly, and in which said tape fastener is located intermediate the end edge of the absorbent pad and the end edge of the pad assembly.

14. The diaper of claim 13 wherein the absorbent pad has a side edge located adjacent the side edge of the pad assembly.

15. The diaper of claim 1 wherein said opening means comprises a pair of spaced openings spaced laterally across the first end section of the tape strip.

16. The diaper of claim 1 wherein the second surface of the sheet has a relatively high affinity for adhesive on the tape strip.

17. The diaper of claim 1 including a release sheet releasably attached to the adhesive on the second section of the tape strip.

18. A disposable diaper, comprising:
   an absorbent pad assembly having a back surface, a front surface, at least one side edge, and opening means extending through the pad assembly, said opening means being spaced from the side edge of the pad assembly; and
   a tape fastener comprising,
      a pressure-sensitive tape strip having a first end section secured to the back surface of the pad assembly with adhesive on the first end section being exposed through said opening means of the pad assembly, and a second securement end section extending past the side edge of the pad assembly, and
      a release sheet having a first surface providing a relatively low affinity for adhesive on said tape strip and a second surface facing the front surface of the pad assembly and having a relatively high affinity for adhesive on said tape strip, with said adhesive exposed through the opening means contacting the second surface of the release sheet adjacent one end of the release sheet and retaining said one end of the release sheet against the pad assembly, said release sheet extending past the side edge of the pad assembly with the second surface of the other end of the release sheet being secured to adhesive on the second end section of the tape strip adjacent the side edge of the pad assembly, said second end section of the tape strip being folded over and releasably attached to the first surface of the release sheet.

19. A disposable diaper, comprising:
   an absorbent pad assembly having a back surface, a front surface, at least one side edge, first opening means extending through the pad assembly and being spaced from the side edge of the pad assembly, and second opening means extending through the pad assembly and being located adjacent the side edge of the pad assembly; and a tape fastener comprising, a pressure-sensitive tape strip having a first end section secured to the back surface of the pad assembly with adhesive on the first end section being exposed through the first and second opening means of the pad assembly, and a second securement end section extending past the side edge of the pad assembly, and a release sheet having a first surface providing a relatively low affinity for adhesive on said tape strip and a second surface facing the front surface of the pad assembly and having a relatively low affinity for adhesive on said tape strip, with said adhesive exposed through the first and second opening means contacting the second surface of the release sheet and retaining the ends of the release sheet against the pad assembly, said second end section of the tape strip being folded over and releasably attached to the first surface of the release sheet.

20. A tape fastener for a disposable diaper having opposed surfaces and opening means extending through the diaper, comprising:

a pressure-sensitive tape strip having a first portion secured to one of the surfaces of the diaper with adhesive on the first portion being exposed through the opening means; and a release sheet having at least a portion secured to the other surface of the diaper by the adhesive exposed through said opening means.

* * * * *

UNITED STATES PATENT AND TRADEMARK OFFICE
CERTIFICATE OF CORRECTION

PATENT NO. : 3,948,258
DATED : April 6, 1976
INVENTOR(S) : Hamzeh Karami

It is certified that error appears in the above-identified patent and that said Letters Patent are hereby corrected as shown below:

At column 7, line 14, change "low" to -- high -- .

Signed and Sealed this

Thirteenth Day of July 1976

[SEAL]

Attest:

RUTH C. MASON
*Attesting Officer*

C. MARSHALL DANN
*Commissioner of Patents and Trademarks*